United States Patent [19]
Müller-Lierheim

[11] Patent Number: 6,056,114
[45] Date of Patent: May 2, 2000

[54] ARRANGEMENT FOR THE CARE OF CONTACT LENSES

[75] Inventor: Wolfgang G. K. Müller-Lierheim, München, Germany

[73] Assignee: MDLE Medical Device Laboratories Europe GmbH, Memmingen, Germany

[21] Appl. No.: 09/215,345

[22] Filed: Dec. 18, 1998

[30] Foreign Application Priority Data

Dec. 22, 1997 [DE] Germany .......................... 197 57 356

[51] Int. Cl.⁷ .................................................. B65D 3/04
[52] U.S. Cl. ......................................... 206/5.1; 206/210
[58] Field of Search ................... 206/5.1, 210; 134/901; 422/28, 30

[56] References Cited

U.S. PATENT DOCUMENTS

| | | |
|---|---|---|
| 4,889,693 | 12/1989 | Su et al. . |
| 4,909,382 | 3/1990 | Cuppari ..................................... 206/5.1 |
| 4,996,027 | 2/1991 | Kanner . |
| 5,164,166 | 11/1992 | Stepanski et al. ........................ 206/5.1 |
| 5,341,879 | 8/1994 | Heyl et al. ................................ 422/30 |
| 5,468,448 | 11/1995 | Nicolsm et al. ........................... 422/30 |
| 5,690,211 | 11/1997 | Jao et al. .................................. 206/5.1 |

FOREIGN PATENT DOCUMENTS

| | | |
|---|---|---|
| 0049767 | 4/1982 | European Pat. Off. . |
| 2425714 | 7/1979 | Germany . |
| 3230231 | 3/1983 | Germany . |
| 19624095 | 9/1997 | Germany . |
| 631248 | 12/1961 | Italy ........................................ 206/5.1 |
| 2209845 | 5/1989 | United Kingdom . |

*Primary Examiner*—David T. Fidei
*Attorney, Agent, or Firm*—Evenson, McKeown, Edwards & Lenahan, P.L.L.C.

[57] ABSTRACT

An arrangement is provided for the care of contact lenses. The arrangement has at least one cup-shaped container made of glass. An interior side of the container carries a platinum layer. The container is exchangeably insertable into a housing, and an $H_2O_2$ care solution is chargeable into the container. A lid is connected in a gastight manner with the housing during closing.

20 Claims, 1 Drawing Sheet

ARRANGEMENT FOR THE CARE OF CONTACT LENSES

BACKGROUND OF THE INVENTION

1. Field of the Invention

This invention relates to an arrangement for the care of contact lenses having at least one container made of glass. A platinum layer is applied to an interior side of the container, and an aqueous $H_2O_2$ care solution can be filled into the container for sterilization and/or disinfection. A lid is provided for closing the container.

2. Description of Related Art

An arrangement of this type is known from German Patent Document DE 196 24 095 C1. In addition, as is known from German Patent Document DE 24 25 714 B2, contact lenses, particularly soft contact lenses, can be sterilized by hydrogen peroxide in an aqueous solution such as a 3%-aqueous hydrogen peroxide solution. The hydrogen peroxide residue is decomposed by a decomposition catalyst into water and oxygen for removal. In this decomposition, the platinum layer in the container, which is known from German Patent Document DE 196 24 095 C1, acts as the catalyst. Gases are formed during the care of the contact lenses and the catalytic decomposition of the hydrogen peroxide.

An arrangement for the care of contact lenses of this type is also known from U.S. Pat. No. 4,889,693. In this arrangement, openings for the escape of the forming gas are provided in a lid which can be screwed onto a container. In an arrangement known from German Patent Document 32 30 231 A1, openings are provided in a container through which gas can escape. In an area of the openings, a covering is provided; this covering is permeable to steam but forms a blockage which is impermeable to liquid. It is known from British Patent Document GB 2 209 845 to provide a pressure control valve for the escape of forming gases in a container. The arrangement known from U.S. Pat. No. 4,996,027 has a sealing device provided between an upper edge of a container and a screwed-on lid. The sealing device is deformed when gas pressure is created so that excess gas can escape. In the known arrangements, the lids are screwed onto the container into which the aqueous $H_2O_2$ care solution is filled. Liquid particles entrained during exiting of the gas appear toward the outside.

SUMMARY OF THE INVENTION

It is one object of the invention to provide an arrangement of the initially mentioned type which offers simple handling and in which the gases formed during contact lens care and neutralization of the care solution can escape without impairing the outside appearance of the arrangement.

According to the invention, this object is achieved by an arrangement which has a housing into which the container can be exchangeably inserted in a receiving compartment. During closing, a lid is connected with the housing in a gastight manner, and a space for a gas passage is provided between an upper edge of the container and an interior side of the lid as well as between an exterior side of the container and an interior side of the receiving compartment.

The housing is constructed such that gas can escape to the outside of the housing. On its underside, the housing can have a bottom which is snapped on, slid on or otherwise fastened. A gap remains between the housing and the bottom through which the gas can escape. The housing preferably consists of plastic.

The lid, which may be screwable onto the housing, may consist of plastic. The screwed connection between the housing and the lid achieves a gastight closure over the glass container in which contact lens care takes place in the $H_2O_2$ care solution. Screw threads for the threaded connection between the lid and the housing are provided on the interior side of the lid on a surrounding edge and on an edge which is upright on the housing and surrounds the opening of the receiving compartment. The preferably cup-shaped container and the receiving compartment preferably have a circular cross-section, with the inside diameter of the receiving compartment having larger dimensions than the outside diameter of the container. The upper edge of the container inserted in the receiving compartment may be situated slightly lower than the upper edge surrounding the receiving compartment on the housing which has the thread. As a result, as in the case of an overflow, escape of the gas is permitted from the glass container. No separate gas removal openings or valves need to be provided on the lid and on the housing.

The platinum layer is preferably applied to the interior of the glass container by sputtering. The platinum layer may be constructed as described in German Patent Document DE 196 24 095 C1 and preferably develops a long-lasting preservation effect beyond neutralization of the hydrogen peroxide. In addition to the desired disinfecting effect of the $H_2O_2$ care agent in the form of the aqueous solution, microorganism growth after neutralization of the solution is avoided. This results from dissolving such an amount of platinum out of the thin sputtered-on platinum layer that the solution has the effect of a preserving solution. Consequently, the lens can be stored in the solution for a long time. Advantageously, an antimicrobial or "oligodynamic" effect is achieved in the neutralized care solution. The addition of a preservative, therefore, is not required.

The particularly cup-shaped container with the platinum layer can be exchanged when a new supply bottle with the $H_2O_2$ care solution is used. A cup-shaped container, in which the care of two contact lenses can take place, may be added to each supply bottle. Two containers respectively for one contact lens may also be added for forming a care device set. Naturally, it is also possible to keep the container or the two containers with the housing together with the supply bottle available as a care device set.

BRIEF DESCRIPTION OF THE DRAWINGS

The present invention will be explained in detail with reference to the drawings.

DESCRIPTION OF THE PREFERRED EMBODIMENTS

Figure 1:
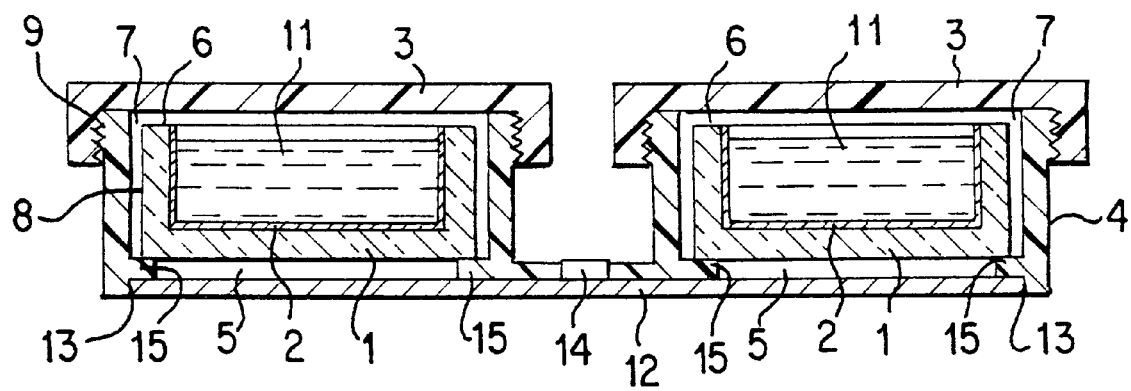
FIG. 1 is a view of a first embodiment of the invention.
Figure 2:
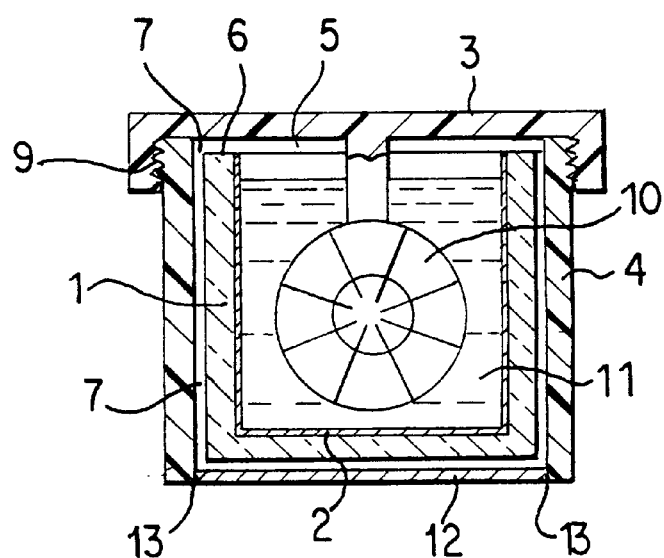
FIG. 2 is a view of a second embodiment of the invention.

The two embodiments of FIGS. 1 and 2 are schematic sectional representations. In the first embodiment of FIG. 1, two cup-shaped containers 1 made of glass, which are impermeable to liquid, are arranged, within a housing 4, in two receiving compartments 5 of the housing. In the embodiment of FIG. 2, one glass container 1 is situated in the housing 4 in the receiving compartment 5. On an exterior side of each receiving compartment 5, a screw thread is provided at the upper edge. In addition, a screw thread is provided on the interior side of each lid. A screwed connection 9 establishes a gastight connection between the lid and the housing 4.

Inside the receiving compartments 5, the respective containers 1 are held at a distance from an underside of the lid 3 and from an interior surface of the respective receiving compartment 5. This results in a space or spaces 7, which form a passage or passages for gases formed in the respective containers 1 during contact lens care. Each of the spaces is formed between respective upper edge 6 of a container 1 and between an exterior side of the container and an interior side of a respective receiving compartment 5.

A bottom 12 is provided on the underside on the respective housing 4. While the housing 4 may consist of plastic, the bottom 12 preferably consists of metal or a metallized plastic. When the contact lenses are placed in the eyes or are taken out of the eyes, the bottom can be used as a mirror. The bottom 12 can be connected with the housing 4 by a snap-type connection 14. As a result of the snap-type connection or a similar connection, gas passage gaps 13 may exist between a surrounding edge of the bottom 12 and the housing 4. This ensures that gas, formed during the contact lens care or during storage of a contact lens in an aqueous care solution 11 in the container 10 and escaping through the spaces 7 from the respective containers 1, can escape to the outside through the gas passage gaps 13.

Spacers 8 and support projections 15 are provided at angular distances from one another on the interior surface of the receiving compartment 5. These spacers and support projections hold the containers 1 made of glass in the respective receiving compartments 5 of the housing 4.

The glass containers 1 may also be constructed with a rounded bottom as known, for example, from European Patent Document EP 0 049 767 A2 in the case of plastic containers which are tightly or firmly inserted into the housing.

On its interior side, the glass container 1 is provided, completely or partially, with a platinum layer 2. This platinum layer 2 may be equipped as known from German Patent Document DE 196 24 095. The platinum layer acts as a decomposition catalyst for the aqueous care solution 11 which, in the case of the illustrated embodiments, is an aqueous $H_2O_2$ care solution. In a known manner, the hydrogen peroxide solution may be a 3% $H_2O_2$ solution. The immersed contact lenses are sterilized and disinfected by the effect of this care solution. In order to avoid hydrogen peroxide residues on the contact lenses after care, by the effect of the platinum layer 2, the hydrogen peroxide is decomposed into hydrogen and oxygen (neutralized). After this neutralization, the platinum layer, which was preferably applied by sputtering to the surface of the glass container 1 and which may have been roughened, has an antimicrobial (oligodynamic) effect so that the neutralized solution, in cooperation with the platinum layer, forms a preservation system for stored lenses.

The respective glass containers 1 with the sputtered-on platinum layers 2 may also be used as a care device set optionally with the containers 4 together with a supply vessel in which the 3% $H_2O_2$ care solution is situated.

In the embodiment of FIG. 1, two glass containers 1 are provided for the care of the two contact lenses. In the embodiment of FIG. 2, however, the two contact lenses in a lens holder 10, which may be fastened to the underside of the lid 3, are immersed in the aqueous care solution 11 in the glass container 2.

For immersing the lenses in the $H_2O_2$ care solution, the lens holder 10 may be constructed in the shape of small baskets which accommodate the lenses receiving care. However, several projections, for example, in the form of pegs, may also be provided on the underside of the lid. An immersion of the lenses into the care solution 11 is ensured by such projections.

In the embodiment illustrated in FIG. 1, projections or a profile, which has a star shape and projects downward in a dome-shaped manner, may be provided on the underside of the respective lid 3. Such is known from European Patent Document EP 0 049 767.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Arrangement for the care of contact lenses, comprising:
   at least one container made of glass having an interior surface to which a platinum layer is applied,
   an aqueous $H_2O_2$ care solution, which can be filled into the container, for the care of contact lenses by sterilization and/or disinfection,
   a separate housing with a receiving compartment into which the container is inserted in an exchangeable manner, and
   a lid for closing the compartment,
   wherein a releasable gastight connection is arranged between the lid and the housing, including the receiving compartment in which the glass container is arranged, and a space for a gas passage is provided between an upper edge of the container and the lid as well as between an exterior side of the container and an interior side of the receiving compartment.

2. Arrangement according to claim 1, wherein the housing has a removable bottom and a gas passage gap is formed in an area of a circumferential edge of the removable bottom between the removable bottom and the housing.

3. Arrangement according to claim 1, and further comprising a screw connection arranged so that the lid can be screwed onto the housing, said screw connection located between the lid and the housing comprising the receiving compartment in which the glass container is arranged.

4. Arrangement according to claim 1, wherein at least one of the lid and the housing consists of plastic.

5. Arrangement according to claim 2, wherein the bottom consists of metal.

6. Arrangement according to claim 1, wherein said at least one container is an exchangeable glass container provided in the housing.

7. Arrangement according to claim 1, wherein the platinum layer is applied by sputtering to the interior surface of the container and wherein a quantity having a preserving effect, which inhibits microbial growth, is delivered into the $H_2O_2$ care solution catalytically neutralized by the platinum layer.

8. Arrangement according to claim 1, wherein a care device set is formed by a storage vessel for the $H_2O_2$ care solution and said at least one container which can be inserted into the housing, said at least one container being glass.

9. Arrangement according to claim 1, and further comprising devices provided on an underside of the lid for immersing the contact lenses in the $H_2O_2$ care solution.

10. Arrangement according to claim 2, and further comprising a screw connection arranged so that the lid can be screwed onto the housing, said screw connection located between the lid and the housing comprising the receiving compartment in which the glass container is arranged.

11. Arrangement according to claim 2, wherein at least one of the lid and the housing consists of plastic.

12. Arrangement according to claim 3, wherein at least one of the lid and the housing consists of plastic.

13. Arrangement according to claim 11, wherein the bottom consists of metal.

14. Arrangement according to claim 2, wherein said at least one container is an exchangeable glass container provided in the housing.

15. Arrangement according to claim 3, wherein said at least one container is an exchangeable glass container provided in the housing.

16. Arrangement according to claim 4, wherein said at least one container is an exchangeable glass container provided in the housing.

17. Arrangement according to claim 2, wherein the platinum layer is applied by sputtering to the interior surface of the container and wherein a quantity having a preserving effect, which inhibits microbial growth, is delivered into the $H_2O_2$ care solution catalytically neutralized by the platinum layer.

18. Arrangement according to claim 3, wherein the platinum If layer is applied by sputtering to the interior surface of the container and wherein a quantity having a preserving effect, which inhibits microbial growth, is delivered into the $H_2O_2$ care solution catalytically neutralized by the platinum layer.

19. Arrangement according to claim 4, wherein the platinum layer is applied by sputtering to the interior surface of the container and wherein a quantity having a preserving effect, which inhibits microbial growth, is delivered into the $H_2O_2$ care solution catalytically neutralized by the platinum layer.

20. Arrangement according to claim 5, wherein the platinum layer is applied by sputtering to the interior surface of the container and wherein a quantity having a preserving effect, which inhibits microbial growth, is delivered into the $H_2O_2$ care solution catalytically neutralized by the platinum layer.

* * * * *